DEFENSIVE PUBLICATION

UNITED STATES PATENT OFFICE

Published at the request of the applicant or owner in accordance with the Notice of Dec. 16, 1969, 869 O.G. 687. The abstracts of Defensive Publication applications are identified by distinctly numbered series and are arranged chronologically. The heading of each abstract indicates the number of pages of specification, including claims and sheets of drawings contained in the application as originally filed. The files of these applications are available to the public for inspection and reproduction may be purchased for 30 cents a sheet.

Defensive Publication applications have not been examined as to the merits of alleged invention. The Patent Office makes no assertion as to the novelty of the disclosed subject matter.

PUBLISHED MARCH 14, 1972

896 O.G. 422

T896,030

APPARATUS FOR THE CONTINUOUS TRANSESTERIFICATION OF AROMATIC DICARBOXYLIC ACIDS WITH DIOLS

Hans Westermann, Walter Meckstroth, Horst-Dieter Bures, and Hans-Ernst Zobel, Marl, and Joachim Bergmann, Gladbeck, Germany, assignors to Eastman Kodak Company, Rochester, N.Y.

Filed Mar. 8, 1971, Ser. No. 121,953

Claims priority, application Germany, Mar. 18, 1970, 20128078

Int. Cl. B01j *1/00;* C07c *69/82*

U.S. Cl. 23—260

1 Sheet Drawing. 15 Pages Specification

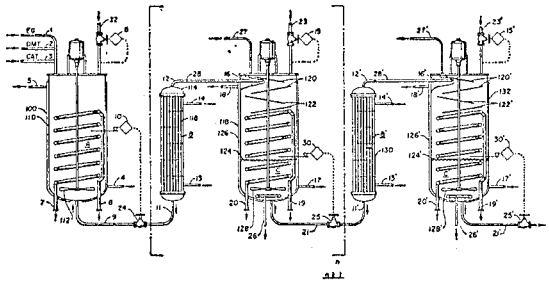

Apparatus for continuous transesterification of dialkyl esters of aromatic dicarboxylic acids with diols including an initial reactor establishing a stirring zone within which reaction takes place followed by an initial reactor arrangement including a heated second reactor estabilshing a tubular zone within which reaction takes place without back-mixing of the reaction materials and a third reactor establishing a stirring zone within which reaction takes place and separation of vaporous by-products occurs, the resulting reacted material entering at least one other reactor arrangement including a heated reactor establishing a tubular zone within which further reaction takes place without backmixing of the materials and the temperature of the materials is further increased and another reactor establishing a stirring zone within which still further reaction takes place and a separation of vaporous by-products occurs, each of the reactor zones adapted to be operated under different temperatures and each of the reactor arrangements and the initial reactor adapted to be operated under different pressures whereby the pressure and temperature conditions are modified depending on the reaction rates desired.

March 14, 1972 H. WESTERMANN ET AL T896,030
APPARATUS FOR THE CONTINUOUS TRANSESTERIFICATION OF AROMATIC DICARBOXYLIC ACIDS WITH DIOLS
Filed March 8, 1971
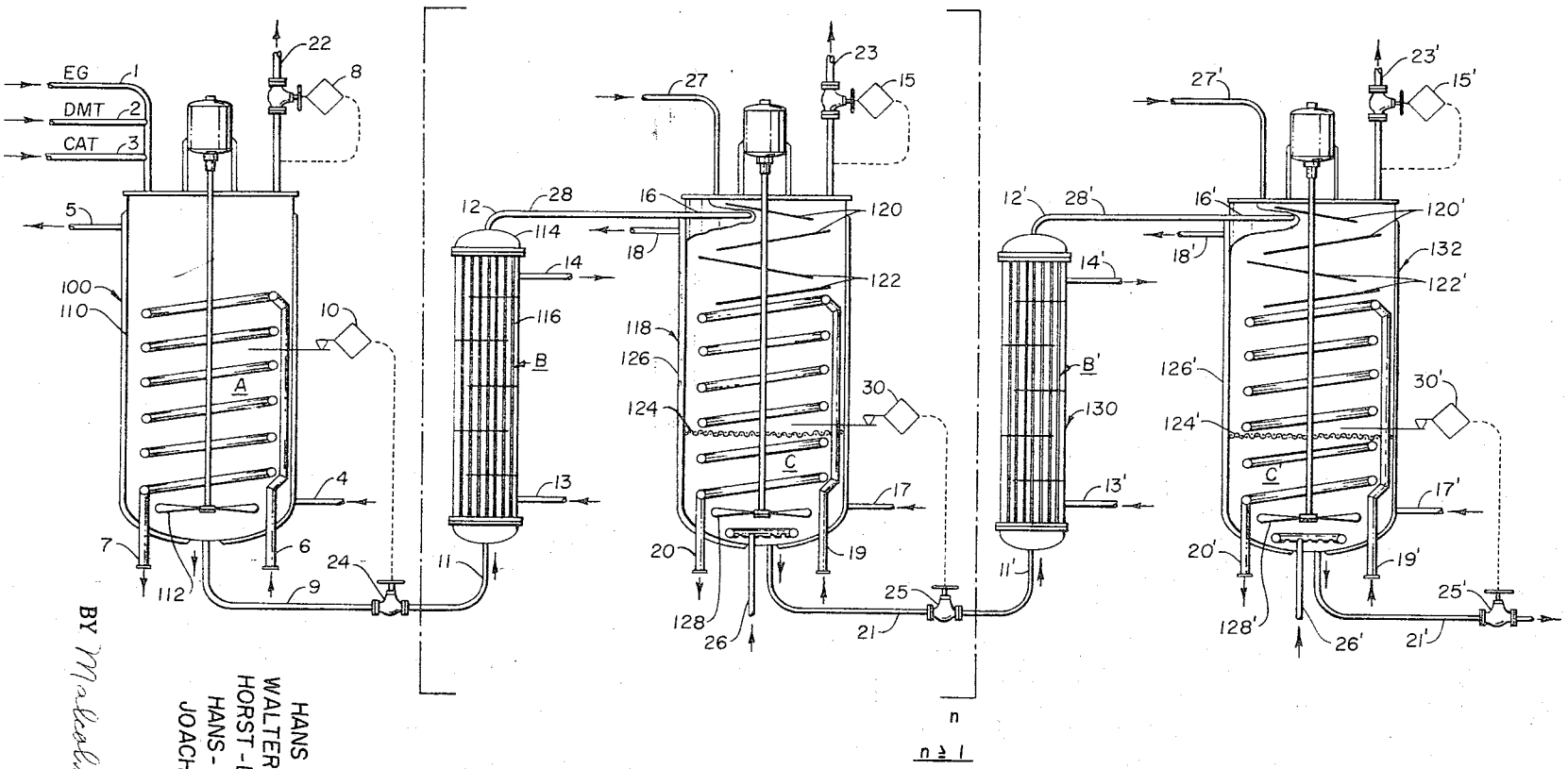
HANS WESTERMANN
WALTER MECKSTROTH
HORST-DIETER BURES
HANS-ERNST ZOBEL
JOACHIM BERGMANN
INVENTORS
BY Malcolm G. Dunn
ATTORNEY